(12) United States Patent
Zhang et al.

(10) Patent No.: US 8,287,840 B2
(45) Date of Patent: Oct. 16, 2012

(54) METHOD OF TREATING MALIGNANT SOLID TUMORS USING TRANSCATHETER ARTERIAL CHEMOEMBOLIZATION (TACE)

(75) Inventors: Liangxuan Zhang, Palo Alto, CA (US); Florencia Lim, Union City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 463 days.

(21) Appl. No.: 12/509,338

(22) Filed: Jul. 24, 2009

(65) Prior Publication Data

US 2011/0020427 A1    Jan. 27, 2011

(51) Int. Cl.
*A61K 51/00*    (2006.01)
*A61M 36/14*    (2006.01)

(52) U.S. Cl. .................. 424/1.33; 424/1.11; 424/1.29; 424/1.65

(58) Field of Classification Search .............. 424/1.11, 424/1.65, 9.1, 9.2, 400, 422, 423, 424, 425, 424/426, 450, 455, 456, 457, 484, 485, 486, 424/489, 490, 491, 492, 497, 499, 500, 1.29, 424/1.33, 1.37, 1.61, 1.81
See application file for complete search history.

(56) References Cited

U.S. PATENT DOCUMENTS 6,589,549 B2 *  7/2003  Shih et al. ................ 424/426

OTHER PUBLICATIONS

Berkland et al., "Fabrication of PLG microspheres with precisely controlled and monodisperse size distributions", J. of Contr. Release 73, pp. 59-74 (2001).
Guan et al., "Interventional treatments for hepatocellular carcinoma", Hep. Pancreat. Dis. Int. vol. 5, No. 4, pp. 495-500 (2006).
Kettenbach et al., "Drug-Loaded Microspheres for the Treatment of Liver Cancer: Review of Current Results", Cardiovasc. Intervent. Radiol. 31, pp. 468-476 (2008).
Liapi et al., "Ttranscatheter and Ablative Therapeutic approaches for Solid Malignancies", J. of Clin. Onc. vol. 25, No. 8, pp. 978-986, (2007).
Lorenceau et al., "Generation of Polymerosomes from Double-Emulsions", Langmuir 21, pp. 9183-9186 (2005).
Pautot et al., "Production of Unilamellar Vesicles Using an Inverted Emulsion", Langmuir 19, pp. 2870-2879 (2003).
Raoul "Natural History of Hepatocellular Carcinoma and Currrent Treatment Optlions", Elsevier Inc. pp. S13-S18 (2008).
Varela et al., "Chemoembolization of hepatocellular carcinoma with drug eluting beads: Efficacy and doxorubicin pharmacokinetics", J. of Hepatology 46, pp. 474-481 (2007).

* cited by examiner

*Primary Examiner* — Dameron Levest Jones
(74) *Attorney, Agent, or Firm* — Squire Sanders (US) LLP; Randy Shen, Esq.

(57) ABSTRACT

This invention is directed to methods of treating solid tumor cancers, particularly refractory cancers by administration of two pluralities of microparticles, one comprising drug-carrying microparticles sized to lodge at the tumor preferably in the capillary bed of the tumor and the other comprising non-drug-carrying microparticles sized to lodge in the arterial system servicing the tumor so as to embolize the tumor.

22 Claims, No Drawings

METHOD OF TREATING MALIGNANT SOLID TUMORS USING TRANSCATHETER ARTERIAL CHEMOEMBOLIZATION (TACE)

FIELD

This invention relates to medicine, cancer, chemotherapy, materials science and medical devices. In particular it relates to a method of treating solid tumors, especially hepatocellular carcinomas using an improved TACE procedure.

BACKGROUND

Cancer is currently the second greatest cause of death in the United States behind coronary heart disease. Even though there is trend toward lower death rates from cancer in the U.S., it has been estimated that the annual personal and financial cost of cancer will be $1.62 trillion dollars by 2017. Further, according to the World Health Organization cancer is set to become the leading cause of death world-wide by 2010.

A particularly nefarious cancer is hepatocellular carcinoma (HCC). This is a primary liver cancer as opposed to a secondary or metastatic liver cancer that begins in another organ and migrates to the liver. HCC accounts for 80 to 90% of liver cancers and occurs in men more than women and is usually seen in patients between about 50 and 60 years old. It is more prevalent in Africa and Asia than the Americas and Europe. Its reputation is due not so much to any particular virulence compared to other solid tumor cancers but rather to the fact that it is rarely diagnosed at an early stage of development and when it is discovered, most chemotherapies and radiation treatment are usually ineffective. Surgery is the only recourse but even then it is very difficult to completely remove the entire tumor; the 5-year survival rate for patients with resectable HCCs is 60%, which is low by current standards. For unresectable tumors the prognosis is extremely poor: the disease is usually deadly within 3-6 months of diagnosis.

The currently preferred treatment for unresectable HCC, which is thought to extend the lifespan of a patient to 1-2 years, is transcatheter arterial chemoembolization (TACE). TACE is implemented in two ways. In the first, a drug is administered in a sterile drip into a selected artery servicing the tumor. After the drug has been administered over a period of time, usually about 30 minutes, microparticles such as gelfoam are infused into the artery to cut off the flow of blood to the tumor. In the second procedure, the chemotherapeutic agent itself is loaded onto microbeads which then are infused into the artery where they serve both to block blood flow and to deliver the drug.

The currently preferred treatment for unresectable HCC, which is thought to extend the lifespan of a patient to 1-2 years, is transcatheter arterial chemoemolization (TACE). TACE is implemented in two ways. In the first, a drug is administered in a sterile drip into a selected artery servicing the tumor. After the drug has been administered over a period of time, usually about 30 minutes, microparticles such as gelfoam are infused into the artery to cut off the flow of blood to the tumor. In the second procedure, the chemotherapeutic agent itself is loaded onto microbeads which then are infused into the artery where they serve both to block blood flow and to deliver the drug.

The problem is that by either of the above methods the drug concentration reaches a maximum in serum, i.e., blood in the vicinity of the tumor, within about 5 minutes of administration. It then drops to a baseline level within about 24 hours. Because of the variation in the drug concentration, TACE must presently be repeated every 4 to 12 weeks.

What is needed is a method for applying TACE in a manner such that a single application of the procedure lasts for a prolonged period, preferably at least 6 months or more. The current invention provides such a method.

SUMMARY

Thus, in one aspect the current invention relates to a method, comprising; identifying a malignant solid tumor in a patient; providing a plurality of first biodegradable microparticles comprising a chemotherapeutic agent, wherein the first plurality of microparticles have a mean diameter of about 10 to 300 µm; delivering the first plurality of microparticles through an artery to a first location at or near the tumor; providing a second plurality of biodegradable microparticles, wherein the second plurality of microparticles have a mean diameter of about 900 to about 1200 µm; and delivering the second plurality of microparticles through the artery to a second location proximal to the location at which the first plurality of particles was delivered, wherein a therapeutically effective amount of the chemotherapeutic agent is released as the first plurality of microparticles degrades over a period of at least 6 months while the second plurality of microparticles substantially completely cuts off the flow of blood to the tumor upon initial delivery to its location and as it degrades over the same time-span as the first plurality of microparticles, blood flow is restored.

In an aspect of this invention, the first and second plurality of microparticles independently comprise a polymer that undergoes about 50% to about 100% mass loss in vivo at about 6 months after delivery at or near the tumor.

In an aspect of this invention, the first and second plurality of microparticles independent comprise a polymer that undergoes about 70% to about 80% mass loss in vivo at about 6 months after delivery of the microparticles at or near the tumor.

In an aspect of this invention, the first plurality of microparticles comprise liposomes.

In an aspect of this invention, the first plurality of microparticles comprise polymersomes.

In an aspect of this invention, the first plurality of microparticles comprise solid polymeric particles.

In an aspect of this invention, the first and second plurality of microparticles independently comprise a polymer selected from the group consisting of poly(D,L-lactide), poly(D,L-lactide-co-glycolide), poly(L-lactide-co-glycolide), poly(L-lactide-co-glycolide-co-ε-caprolactone) and poly(D,L-lactide-co-ethylene glycol), poly(L-lactide-co-ethylene glycol), poly(D, L-lactide-bl-glycolide), poly(L-lactide-bl-glycolide), poly(D,L-lactide-bl-ethylene glycol), poly(L-lactide-bl-glycolide), poly(D,L-lactide-bl-glycolide-bl-caprolactone), poly(L-lactide-bl-glycolide-bl-ethylene glycol, a poly(ester amide) and any combination thereof.

In an aspect of this invention, the first plurality of microparticles comprises poly(L-lactide-co-glycolide).

In an aspect of this invention, the molar ratio of L-lactide to glycolide is about 3:2 to about 9:1.

In an aspect of this invention, the number average molecular weight of the poly(L-lactide-co-glycolide) is about 100 kDa to about 150 kDA.

In an aspect of this invention, the first plurality of microparticles comprises a polymer comprising poly(ethylene glycol).

In an aspect of this invention, the number average molecular weight of poly(ethylene glycol) in any of the poly(ethylene glycol)-containing polymers is about 500 kDa to about 10,000 kDa.

In an aspect of this invention, the chemotherapeutic drug to polymer weight ratio is about 1:1 to about 1:5.

In an aspect of this invention, two or more chemotherapeutic agents are loaded into or onto the same first microparticles.

In an aspect of this invention, two or more chemotherapeutic agents are loaded into or onto different first microparticles, the different first microparticles being mixed together prior to delivery at or near the tumor.

In an aspect of this invention, the malignant solid tumor is a hepatocellular carcinoma.

In an aspect of this invention, the chemotherapeutic agent is doxorubicin.

In an aspect of this invention, the chemotherapeutic agent further comprises an agent selected from the group consisting of cisplatin and mitomycin C.

In an aspect of this invention, the second plurality of microparticles comprise solid polymeric particles.

In an aspect of this invention, the first plurality of microparticles is delivered at or near the tumor prior to delivery of the second plurality of microparticles, or the second plurality of microparticles is delivered at or near the tumor after which the first plurality of microparticles is injected into the artery between the tumor and where the second plurality of microparticles have lodged in the artery.

DETAILED DESCRIPTION

It is understood that use of the singular throughout this application including the claims includes the plural and vice versa unless expressly stated otherwise. That is, "a" and "the" are to be construed as referring to one or more of whatever the word modifies. Non-limiting examples are: "a therapeutic agent," which is understood to include one such agent, two such agents or, under the right circumstances, as determined by those skilled in the treatment of diseased tissues, even more such agents unless it is expressly stated or is unambiguously obvious from the context that such is not intended. Likewise, "a biodegradable polymer" refers to a single polymer or a mixture of two or more polymers unless, again, it is expressly stated or absolutely obvious from the context that such is not intended.

As used herein, unless specified otherwise, any words of approximation such as without limitation, "about," "essentially," "substantially" and the like mean that the element so modified need not be exactly what is described but can vary from exact compliance with the written description by as much as ±15% without exceeding the scope of this invention. Thus, for example without limitation, to stop the flow of blood through an artery "substantially completely" means to cut off at least 85% of the flow of blood.

The target tissue of this invention is a malignant solid tumor. A solid tumor refers to an abnormal mass of tissue that usually does not contain cysts or liquid areas. A tumor that is not cancerous is described as "benign" while a cancerous tumor, the targets of this invention, are termed "malignant." Different types of solid tumors are named for the particular cells that form them, for example, sarcomas formed from connective tissue cells (bone cartilage, fat, etc.), carcinomas formed from epithelial tissue cells (breast, colon, pancreas, etc.) and lymphomas formed from lymphatic tissue cells (lymph nodes, spleen, thymus, etc.). Treatment of all types of solid tumors is within the scope of this invention. In particular the target tumor is an HCC.

As used herein, "identifying" a malignant solid tumor simply refers to detecting its presence and its type by any means currently known in the art or as may become known in the future.

As used herein, "chemotherapeutic agent" refers to any substance that, when administered in a therapeutically effective amount to a patient suffering from a solid tumor cancer, has a therapeutic beneficial effect on the health and well-being of the patient. A therapeutic beneficial effect on the health and well-being of a patient includes, but it not limited to: (1) curing the cancer; (2) slowing the progress of the cancer; (3) causing the tumor to retrogress; or (4) alleviating one or more symptoms of the cancer. As used herein, a chemotherapeutic agent also includes any substance that, when administered in a prophylactic amount to a patient afflicted with a solid tumor cancer or who has been rendered substantially free of cancer as the result of one or more therapeutic treatment regimes, has a beneficial effect on the health and well-being of the patient. A prophylactic beneficial effect on the health and well-being of a patient includes, but is not limited to: (1) maintaining the cancer at a retrogressed level once such level has been achieved by a therapeutically effective amount of a substance, which may be the same as or different from the substance used in a prophylactic effective amount; or, (2) preventing or delaying recurrence of the cancer after a course of treatment with a therapeutically effective amount of a substance, which may be the same as or different from the substance used in a prophylactic effective amount, has concluded. It is presently preferred that, when the solid tumor is an HCC, the chemotherapeutic agent comprises at least doxorubicin. Any other chemotherapeutic that has a beneficial effect on the HCC may be combined with the doxorubicin but at present cisplatin and mitomycin C are preferred co-therapeutic agents to be administered with doxorubicin.

A "therapeutically effective amount" refers to that amount of a chemotherapeutic agent that will have a beneficial effect, which may be curative or palliative, on the health and well-being of the patient so afflicted. A therapeutically effective amount may be administered as a single bolus, as intermittent bolus charges, as short, medium or long term sustained release formulations or as any combination of these. As used herein, short-term sustained release refers to the administration of a therapeutically effective amount of a therapeutic agent over a period of about an hour to about 3 days. Medium-term sustained release refers to administration of a therapeutically effective amount of a therapeutic agent over a period of about 3 days to about 4 weeks and long-term refers to the delivery of a therapeutically effective amount over any period in excess of about 4 weeks. Presently, it is preferred that a therapeutically effective amount of the chemotherapeutic agent be delivered over a period of at least 6 months.

As used herein, the use of "preferred," "preferably," or "more preferred," and the like refer to modify an aspect of the invention refers to preferences as they existed at the time of filing of the patent application.

Structural vehicles or "particles" that may be used with the method of this invention include, without limitation, liposomes, biodegradable polymersomes and biodegradable microparticles of a mean size such that at least 80% of them will not be able to pass through the vasculature servicing the target tumor, in particular an HCC. For the purposes of this invention, two different mean particle sizes are employed. One plurality of particles will have a mean size of about 10 nanometers (nm) to about 300 micrometers (µm), these being the drug-delivery particles. The other plurality of particles will have a mean size of about 900 µm to about 1200 µm and will be used to embolize an artery in the vicinity of a tumor being treated. The two pluralities of particles may comprise the same structural vehicle or they may be fabricated of different such vehicles. For example without limitation, the drug-carrying plurality of particles may be liposomes while the embolizing plurality of particles may be polymersomes or solid microparticles.

As used herein, "embolization," embolizing" and any other variations on the term refers to the procedure of introducing an artificial material at a site in a blood vessel such that the material lodges there and blocks the flow of blood. Materials that can be used to embolize a vessel include, without limitation, coils or hydrocoils, particles, foams and plugs but for the purpose of this invention, the structural vehicles mentioned above are preferred.

As used herein, a "liposome" refers to a core-shell structure in which the shell comprises phospholipids or sphingolipids that surround a usually liquid, and in most cases aqueous, core.

Phospholipids are molecules that have two primary regions, a hydrophilic head region comprised of a phosphate of an organic molecule and one or more hydrophobic fatty acid tails. In particular, naturally-occurring phospholipids have a hydrophilic region comprised of choline, glycerol and a phosphate and two hydrophobic regions comprised of fatty acid. When phospholipids are placed in an aqueous environment, the hydrophilic heads come together in a linear configuration with their hydrophobic tails aligned essentially parallel to one another. A second line of molecules then aligns tail-to-tail with the first line as the hydrophobic tails attempt to avoid the aqueous environment. To achieve maximum avoidance of contact with the aqueous environment, i.e., at the edges of the bilayers, while at the same time minimizing the surface area to volume ratio and thereby achieve a minimal energy conformation, the two lines of phospholipids, know as a phospholipid bilayer or a lamella, converge into a sphere and in doing so entrap some of the aqueous medium, and whatever may be dissolved or suspended in it, in the core of the sphere. Examples of phospholipids that may be used to create liposomes are, without limitation, 1,2-dimyristroyl-sn-glycero-3-phosphocholine, 1,2-dilauroyl-sn-glycero-3-phosphocholine, 1,2-distearoyl-sn-glycero-3-phosphocholine, 1,2-dimyristoyl-sn-glycero-3-phosphoethanolamine, 1,2-dipalmitoyl-sn-glycero-3-phosphoethanolamine, 1,2-dioleoyl-sn-glycero-3-phosphate monosodium salt, 1,2-dipalmitoyl-sn-glycero-3-[phosphor-rac-(1-glycerol)]sodium salt, 1,2-dimyristoyl-sn-glycero-3-[phospho-L-serine]sodium salt, 1,2-dioleoyl-sn-glycero-3-phosphoethanolamine-N-glutaryl sodium salt and 1,1',2,2'-tetramyristoyl cardiolipin ammonium salt.

Liposomes may be unilamellar, composed of a single bilayer, or they may be multilamellar, composed of two or more concentric bilayers. Liposomes range from about 20-100 nm diameter for small unilamellar vesicles (SUVs), about 100-5000 nm for large multilamellar vesicles and ultimately to about 100 microns for giant multilamellar vesicles (GMVs). LMVs form spontaneously upon hydration with agitation of dry lipid films/cakes which are generally formed by dissolving a lipid in an organic solvent, coating a vessel wall with the solution and evaporating the solvent. Energy is then applied to convert the LMVs to SUVs, LUVs, etc. The energy can be in the form of, without limitation, sonication, high pressure, elevated temperatures and extrusion to provide smaller single and multi-lamellar vesicles. During this process some of the aqueous medium is entrapped in the vesicle. Generally, however, the fraction of total solute and therefore the amount of therapeutic agent entrapped tends to be rather low, typically in the range of a few percent. Recently, however, liposome preparation by emulsion templating (Pautot, et al., *Langmuir,* 2003, 19:2870) has been shown to result in the entrapment of virtually 100% of aqueous solute. Emulsion templating comprises, in brief, the preparation of a water-in-oil emulsion stabilized by a lipid, layering of the emulsion onto an aqueous phase, centrifugation of the water/oil droplets into the water phase and removal of the oil phase to give a dispersion of unilamellar liposomes. This method can be used to make asymmetric liposomes in which the inner and outer monolayers of the single bilayer contain different lipids. Any of the preceding techniques as well as any others known in the art or as may become known in the future may be used as compositions of therapeutic agents in or on a delivery interface of this invention. Liposomes comprising phospho- and/or sphingolipids may be used to deliver hydrophilic (water-soluble) or precipitated therapeutic compounds encapsulated within the inner liposomal volume and/or to deliver hydrophobic therapeutic agents dispersed within the hydrophobic core of the bilayer membrane.

As used herein, a "microparticle" refers to a solid having as its smallest cross-sectional, i.e., through the solid as opposed to along its surface, dimension about one micron. Presently preferred are microparticles having a mean size of about 10 nm to about 300 µm if intended as the drug-carrying particles or about 900 to about 1200 µm if intended to be the embolizing particles. The solid can have any desired shape such as without limitation spherical, ellipsoid, rod-like, entirely random shaped, etc., although substantially spherical microparticles are well-known in the art, are readily prepared and are presently preferred. The microparticle may be constructed of one or more biocompatible substances and may be porous so as to permit elution of the therapeutic substance embedded in it or may be biodegradable such that as the particle degrades the therapeutic substance is released into the environment.

Particle size distributions may be represented in a number of ways, one of the most common of which is "mean particle size." A "mean" size may refer to a value based on particle length, width and/or diameter, on area or on volume. As used herein, "mean size" is determined by measuring the longest through-particle distance of each microparticle and then dividing by the total number of microparticles. Of course, this requires sophisticated equipment when dealing with the large numbers of microparticles contemplated by this invention but such equipment is well-known and readily available to those skilled in the art and such determination of mean size is commonplace in the art. To assure efficient capture of the microparticles of this invention, not only should the microparticles have the stated mean size, the distribution of particle size should be a narrow as possible, that is as close to monodisperse as can be achieved. No specific size dispersion is presently preferred because the narrower the better and, while several techniques are discussed below for achieving relatively narrow size distributions, as the state of the art advances, equipment and procedures for reaching even narrower size distributions will surely become available and all such equipment, procedures and size distributions will clearly be within the scope of this invention.

A particular method of determining mean particle size is dynamic light scattering ("DLS"), which is also called photon correlation spectroscopy, and which determines the hydrodynamic or Stokes diameter based on diffusion measurements. The hydrodynamic diameter includes solvent associated with the particle. This mean hydrodynamic diameter obtained from DLS is close to the volume-average diameter. One method is outlined in the International Standards Organization ("ISO") 13321. There are many other means of determining mean particle size known to those skilled in the art. Also known to those skilled artisans is the fact that the various means tend to give different results but the correlation of the results of one method to each other method is also well known. Thus, any method of particle size determination may be used but the result should be correlated with that obtained by DLS to assure a mean particle size that will be entrapped at the correct point in the circulatory system, i.e., the capillaries.

With regard to mean size and size distribution, as noted above, it is presently preferred that at least 80% of the particles, be they liposomes, polymersomes or solid microparticles, administered into an artery serving a particular tissue are entrapped at the selected location in the vasculature servicing the target tumor. More preferably, at least 90% of the microparticles will be so entrapped and most preferably at present, at least 99% of the microparticles will be entrapped.

The plurality of particles herein can comprise several different designs. In the simplest, the therapeutic agent is simply encapsulated in the carrier at a single concentration so that all particles are substantially the same with regard to drug load. In another design, the therapeutic agent can be encapsulated in the carrier, or if desired in several different carriers, at different concentrations in separate preparations and the particles formed in those separate preparations can be combined for administration to a patient. In yet another design, different therapeutic agents can be separately encapsulated in a carrier, or, again, in different carriers, at various concentrations, the particles being combined for administration or, if desired, administered sequentially. Two or more therapeutic agents can, of course, be encapsulated in the same particulate carrier such that the resulting particles each contain more than one therapeutic agent. Those skilled in the art will, based on the disclosure herein, be able to devise additional combinations of carrier and therapeutic agent(s); all such combinations are within the scope of this invention.

The selection of the presently preferred range of particle sizes is based on the average diameter of various portions of the vasculature. A basic premise of this invention is that microparticles containing an appropriate therapeutic agent or combination of agents can be administered into an artery that directly services a tissue of interest. By "directly services" is meant that blood flowing through the artery proceeds in one direction only through the labyrinthine maze comprising artery→arterioles→metarterioles→capillaries→postcapillary venules→venules—vein. It is noted that the kidneys have a rather unique circulatory system: arteries →afferent arterioles →glomerular capillaries →efferent arterioles but the methods of this invention are eminently suitable for use with the kidneys as well as other organs. Thus, particles injected into blood in the artery have nowhere to go but into the diseased tissue where, depending on their size, they lodge in whichever of the preceding substructures has a diameter that is smaller than the selected particle mean size. Arterioles are generally regarded as having inside diameters in the range of about 10 to 50 microns, metarterioles about 10 to 20 microns and capillaries approximately 4 to 15 (average about 8) microns in diameter. Thus, microparticles having a mean size of about 10 µm, the smallest size for drug-carrying particles of this invention, should be efficiently trapped at the capillary level. For example, it has been reported that in one experiment 97% of 15 micrometer radiolabeled microspheres injected in an artery servicing the eye were entrapped at the first pass. At the other end of the spectrum for drug-carrying particles, those with a mean size of about 300 µm, these will be entrapped in the main artery in the vicinity of where it necks down to arteriole size.

Entrapping the drug-carrying particles at the capillary level is presently preferred in that it offers the broadest specific application of chemotherapeutic agent to the target tumor assuming the tumor has developed a mature capillary system. This is due to the physiology of the capillary system. That is, the capillary system comprises a vast network of minute (averaging approximately one millimeter in length and 8-10 microns in diameter) vessels that permeates virtually every tissue in the mammalian body. As testament to the ubiquity of capillaries, it has been estimated that their number is approximately 19,000,000,000 and that most living tissue cells lie within 1-3 cell lengths of a capillary. Thus, to achieve maximum dispersion of a therapeutic agent in a target tissue, it makes sense that the vehicle carrying the therapeutic agent be capable of maneuvering through the circulatory system to the capillary level.

On the other hand, if the target tumor has not developed a sophisticated capillary system, it might be preferable to use larger size delivery vehicles/particles that will lodge in larger diameter vessels servicing the capillaries. Such determination is left to the attending physician and should be based on whatever diagnostic evidence is evinced during the course of treatment of the patient.

Whatever the selected mean particle size of the drug delivery vehicles, the mean size of the embolizing particles must be larger so as to substantially or, if desired, completely cut off the flow of blood to the region where the drug-delivery vehicle has lodged. In this manner, drug can be released from the delivery vehicle and have time to enter into the surrounding tissue without the risk of being carried away by the blood.

It may, on the other hand, be desirable to select the embolizing particle size based on the dimensions of the largest artery servicing the tumor that services only or predominantly the tumor. In this manner, stress can be placed on the entire tumor while at the same time embolization of healthy tissues is held to a minimum.

In addition to solid microparticles and liposomes, a particle of this invention may be a polymersome, which is akin to a liposome wherein the shell is made up of synthetic amphiphilic polymers rather than phospholipids and sphigolipids. Examples of polymers that can be used to prepare polymersomes include, without limitation, poly(ethylene glycol)-b-poly(ε-caprolactone), poly(ethylene glycol)-b-polyesters, poly(ethylene glycol)-b-poly(L-aminoacids), poly(N-vinylpyrrolidone)-bl-poly(orthoesters), poly(N-vinylpyrrolidone)-b-polyanhydrides and poly(N-vinylpyrrolidone)-b-poly(alkyl acrylates). Depending on the length and chemical nature of the polymers in the diblock copolymer, polymersomes can be substantially more robust that liposomes. In addition, the ability to control completely the chemical nature of each block of the diblock copolymer permits tuning of the polymersome's composition to fit the desired application. For example, membrane thickness can be controlled by varying the degree of polymerization of the individual blocks. Adjusting the glass transition temperatures of the blocks will affect the fluidity and therefore the permeability of the membrane. Even the mechanism of release can be modified by altering the nature of the polymers.

Polymersomes can be prepared in the same manner as liposomes. That is, a film of the diblock copolymer can be formed by dissolving the copolymer in an organic solvent, applying a film of the copolymer-containing solvent to a vessel surface, removing the solvent to leave a film of the copolymer and then hydrating the film. Polymersomes can also be prepared by dissolving the diblock copolymer in a solvent and then adding a poor solvent for one of the blocks, which will result in the spontaneous formation of polymersomes.

As with liposomes, polymersomes can be used to encapsulate therapeutic agents by including the therapeutic agent in the water used to rehydrate the copolymer film. Polymersomes can also be force-loaded by osmotically driving the therapeutic agent into the core of the vesicle. Also as with liposomes, the loading efficiency is generally low. Recently, however, a technique has been reported that provides polymersomes of relative monodispersity and high loading efficiency; generation of polymersomes from double emulsions. Lorenceau, et al., *Langmuir,* 2005, 21:9183-86. The technique involves the use of microfluidic technology to generate double emulsions consisting of water droplets surrounded by a layer of organic solvent. These droplet-in-a-drop structures are then dispersed in a continuous water phase. The diblock copolymer is dissolved in the organic solvent and self-assembles into proto-polymersomes on the concentric interfaces of the double emulsion. The actual polymersomes are formed by completely evaporating the organic solvent from the shell. By this procedure the size of the polymersomes can be finely controlled and, in addition, the ability to maintain complete separation of the internal fluids from the external fluid throughout the process allows extremely efficient encapsulation. This technique along with any other technique know in the art or as may become known in the future can be used to prepare a composition of therapeutic agents for use in or on a delivery interface of this invention.

As used herein, "delivering" microparticles "at or near" a tumor refers to deposition of the particles in an artery sufficiently close to the target tumor to assure to the extent possible that the first instance of encountering a vessel of sufficiently small internal diameter to prevent passage of the particles will be the capillary system of the tumor itself. Such delivery can be accomplished by a number of means including, without limitation, the use of catheters and direct injection. Both of these methods of delivering microparticles to a specific locale in a patient's body are well-known to those skilled in the art and require no further explication here.

As use herein, "proximal to the location of the first plurality of microparticles" refers to a point in the target artery that is between where the first plurality of microparticles has lodged and the heart so as to substantially cut off the flow of blood past the region with the first plurality of microparticles has lodged.

As mentioned previously, presently preferred delivery vehicles of this invention are microparticles, liposomes and polymersomes having a mean particle size such that the majority of the particles are entrapped in the vascular system at the chosen locale upon the first pass of the plurality of particles through the patient's circulatory system.

As used herein, "first pass" refers to the first time a particle encounters a vessel of the correct inside diameter be it a capillary, an arteriole, etc. With regard, without limitation, to a capillary target, first pass refers to the first time the drug delivery vehicle encounters the capillary bed at the terminus of a selected artery serving a tumor. Microparticles that, for one reason or another, pass through the bed and find their way to venules and thence to veins will continue to circulate in the circulatory system until they once again encounter a capillary bed (although it may not be the capillary bed of the target tissue, which is why it is preferred that as high a percentage as possible are entrapped in the capillary bed of the target diseased tissue after having been administered into an artery serving that tissue). Again, for the purpose of this invention, it is preferred that at least 80% of the microparticles are entrapped at the first pass, more preferably 90% and presently most preferably, 99%.

With regard to embolizing particles, they will clearly be trapped on the first pass since their size renders them incapable of passing through the capillary system to the veins. The critical aspect of these particles is that they interrupt blood flow upstream from where the drug-carrying particles are trapped.

As mentioned above, in order to achieve the preceding degrees of entrapment it is necessary to produce microparticles having a size distribution a narrow as possible around the target mean size wherein the target mean size is determined by the vessel size in the tissue being treated. That is, again with reference to capillary bed entrapment, the mean particle size must be small enough to pass through an arteriole (afferent arteriole in the case of the kidneys) but large enough to be trapped by a capillary. While there may be other means to accomplish this and any such means is within the scope of this invention, presently preferred means include emulsification followed by supercritical fluid solvent extraction, ultrasonic atomization or droplet formation, electrohydrodynamic atomization and membrane emulsification.

Emulsification followed by supercritical fluid solvent extraction to form microparticles having a very narrow size range is a well-known technique in the art and therefore need not be extensively discussed herein, In brief, the technique involves the formation of an emulsion by dissolving a polymer and a therapeutic agent in a solvent for both, adding the solution under high shear to water containing emulsifying agent, sonicating to achieve a narrow droplet size range, passing the droplets through a porous membrane of well-defined pore size and then extracting the solvent from the microparticles using a supercritical fluid to give a hardened particle. A supercritical fluid, that is a fluid above its critical temperature and pressure, is used because of the physical properties of such fluids, which are intermediate between those of a gas those of a liquid. For example, supercritical carbon dioxide has a viscosity in the range of about 0.02 to about 0.1 centipoise (cP) whereas liquids have viscosities 0.5-1.0 cP and gasses have viscosities around 0.01 cP. Further, the diffusivities of solutes in supercritical carbon dioxide are up to a factor of 10 higher than in liquid solvents. This and the tunability of the solvating properties of supercritical fluids, which are a complex (but relatively well-understood) function of pressure and temperature, permit extremely selective extraction of one material, the solvent herein for instance, from others it may be combined with.

In any event, the hardened microparticles obtained after supercritical fluid solvent extraction may then be passed through yet another filter with well-defined pore size to still further control particle size distribution.

Atomization of a solution using an ultrasonic transducer can produce relatively monodisperse droplets. When captured in a appropriate bath and hardened, this can result in a narrow distribution of microspheres. The ultrasonic energy may be applied using a "horn" with the solution either flowing through it or being applied to its surface. The ultrasonic horn oscillates at a fixed frequency supplied by an ultrasonic transducer. Ultrasonic spray nozzles of this sort are readily available from Sono-Tek Corp, Milton, N.Y.

Another technique that produces relatively monodisperse particles involves the use of acoustic excitation of a liquid stream to break the stream up into monodisperse particles (Berkland, et al., J. Control. Rel., 2001, 73:59-74). The liquid stream is composed of a polymer and a therapeutic agent dissolved in one or more solvents. The droplets are carried by a carrier stream to a hardening bath where the solvent is removed. The frequencies needed to excite the liquid stream sufficiently to break it up into droplets are in the ultrasonic region of the spectrum.

Electrohydrodynamic atomization (EDHA) is another, relatively new but nevertheless well-characterized technique in the art for producing narrow size distribution, i.e. essentially monodisperse, microparticles. Again, without going into unnecessary detail since those skilled in the art will be very familiar with the technique, electrohydrodynamic atomization involves pumping a solution through a nozzle wherein a high voltage potential has been established between the tip of the nozzle and a counter-electrode. The high potential causes a build-up of electric charge in droplets at the nozzle tip and when the coulombic forces exceed the surface tension of the droplets, they separate, essentially explode, into smaller droplets. If parameters are optimized to achieve a stable spray, monodispersed droplets are obtained. Removal of solvent from the droplets yields monodisperse solid microparticles. Parameters that may be varied to achieve a particular average size droplet/particle include, without limitation, the applied voltage, the flow rate, density, conductivity and surface tension.

Normal emulsification techniques generally afford droplets of relative polydispersity, at least with regard to the narrow size distribution desired for use in the current invention. Thus, the requirement of one and perhaps two filtrations as set forth above with regard to emulsification/supercritical fluid solvent extraction. This is due primarily to the myriad parameters that come into play when preparing an emulsion such as, without limitation, the concentration of the agents, the nature of the drug/polymer/surfactant/solvent interaction, polymer molecular weight, sonication power, stir speed, fluid dynamics of the system and temperature. These shortcomings, at least with regard to the present invention, can be overcome by using the technique known as membrane emulsification.

Membrane emulsification is another relatively new technique for producing essentially monodisperse microparticles. As with standard emulsification followed by multiple filtrations and electrohydrodynamic atomization, membrane emulsification, while a relatively recent development, is well-known to those skilled in the art and need not be detailed herein. In brief, membrane emulsification involves the injection of an intended discontinuous phase through a porous membrane in which pore size is very carefully controlled into the intended continuous phase, which is moving past the porous membrane on the side opposite that from which the discontinuous phase is being injected. Droplets are sheared off the membrane by the moving continuous phase. Control of droplet size is quite exquisite compared to normal emulsification techniques because size is determined predominantly by easily varied parameters including the speed of the continuous phase, viscosity of the continuous phase, interfacial tension between the phases, the chemistry of the system—surfactant type and physical properties of all the constituents—and, of course, pore size. Newer techniques for creating porous membranes with a very precise pore size such as laser drilling and lithographic procedures have made membrane emulsification even more attractive as a technique for control of particle size distribution.

Any selected particle size can be prepared with relatively narrow mean size distribution using the above techniques, as well as others known in the art, by incorporating well-known mechanical and procedural changes in the methods described.

Polymeric microparticles presently preferred drug delivery vehicles of this invention. The polymer(s) must be biocompatible and can be either biostable or biodegradable. As used herein, biodegradable includes all means by which a polymer can be disposed of in a patient's body, which includes bioabsorption, resorption, etc. Biostable simply means that the polymer does not biodegrade or bioabsorb under physiological conditions over a relatively long period of time that may reach years.

As used herein, "biocompatible" refers to a polymer that both in its intact, that is, as synthesized, state and in its decomposed state, i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

As used herein, "biodegradable" refers to any natural means by which a polymer can be disposed of in a patient's body. This includes such phenomena as, without limitation, biological decomposition, bioerosion, absorption, resorption, etc. Biodegradation of a polymer in vivo results from the action of one or more endogenous biological agents and/or conditions such as, without limitation, enzymes, microbes, cellular components, physiological pH and temperature and the like. Bioabsorbable or bioresorbable on the other hand generally refers to the situation wherein the polymer itself or its degradation products are removed from the body by cellular activity such as, without limitation, phagocytosis. Bioerodible refers to both physical processes such as, without limitation, dissolution and chemical processes such as, without limitation, backbone cleavage by hydrolysis of the bonds linking constitutional units of a polymer together. As used herein, biodegradable includes bioerodible, bioresobable and bioabsorbable.

The biodegradability of a polymer can be characterized by its "mass loss" in vivo over a period of time. By "mass loss" is meant loss in actual weight of a particle fabricated from the polymer a contrasted with "molecular weight loss," which refers to the break-down of individual polymer chains to smaller fragments, a process that generally precedes mass loss when the smaller fragments break off of the polymeric particle.

Physiological conditions merely refers to the physical, chemical and biochemical milieu that constitutes the mammalian body and includes, without limitation, pH, temperature, enzymes and the presence of destructive cells such as phagocytes.

Among biocompatible, relatively biostable polymers useful as carriers for the preparation of microparticles of this invention are, without limitation, polyacrylates, polymethacryates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins.

Biocompatible, biodegradable polymers that can be used for the carrier/particle-forming of this invention include, again without limitation, naturally-occurring polymers such as, without limitation, collagen, chitosan, alginate, fibrin, fibrinogen, cellulosics, starches, dextran, dextrin, hyaluronic acid, heparin, glycosaminoglycans, polysaccharides and elastin.

Synthetic or semi-synthetic biocompatible, biodegradable polymers may also be used as carriers for the purpose of this invention. As used herein, a synthetic polymer refers to one that is created wholly in the laboratory while a semi-synthetic polymer refers to a naturally-occurring polymer than has been chemically modified in the laboratory. Examples of synthetic polymers include, without limitation, polyphosphazines, polyphosphoesters, polyphosphoester urethane, polyester urethanes, polyester urethane ureas, polyhydroxyacids, polyhydroxyalkanoates, polyanhydrides, polyesters, polyorthoesters, polyamino acids, polyoxymethylenes, poly(ester amides) and polyimides.

Further non-limiting examples of biocompatible biodegradable polymers that may be suitable as carriers herein include, without limitation, polycaprolactone, poly(L-lactide), poly(D,L-lactide), poly(D,L-lactide-co-PEG) block copolymers, poly(D,L-lactide-co-trimethylene carbonate), polyglycolide, poly(lactide-co-glycolide), polydioxanone (PDS), polyorthoester, polyanhydride, poly(glycolic acid-co-trimethylene carbonate), polyphosphoester, polyphosphoester urethane, poly(amino acids), polycyanoacrylates, poly(trimethylene carbonate), poly(iminocarbonate), polycarbonates, polyurethanes, copoly(ether-esters) (e.g. PEO/PLA), polyalkylene oxalates, polyphosphazenes, PHA-PEG, and combinations thereof. The PHA may include poly(α-hydroxyacids), poly(β-hydroxyacid) such as poly(3-hydroxybutyrate) (PHB), poly(3-hydroxybutyrate-co-valerate) (PHBV), poly(3-hydroxyprorionate) (PHP), poly(3-hydroxyhexanoate) (PHH), or poly(4-hydroxyacid) such as poly poly(4-hydroxybutyrate), poly(4-hydroxyvalerate), poly(4-hydroxyhexanoate), poly(hydroxyvalerate), poly(tyrosine carbonates), poly(tyrosine arylates), poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline containing polymer, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, methacrylate polymers containing 2-methacryloyloxyethyl-phosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, elastin protein mimetics, or combinations thereof.

Blends and copolymers of the above polymers may also be used and are within the scope of this invention. Based on the disclosures herein, those skilled in the art will recognize those implantable medical devices and those materials from which they may be fabricated that will be useful with the coatings of this invention.

Any reference to the molecular weight of a polymer of this invention is reported as the number average molecule weight, the nature and determination of which is well-known in the art and need not be explicated further here.

As used herein, The "weight ratio" of a chemotherapeutic drug to a polymer refers to quantity of the drug relative to the quantity of polymer that constitutes the microparticle carrying the drug in like units, e.g. without limitation, mg:mg so that, for instance, a drug to polymer weight ratio of 1:5 would mean that the amount of drug in or on a microparticle in which the polymer component weights 5 mg would be 1 mg.

As noted previously, a chemotherapeutic agent may be administered to a patient using the method of this invention in a bolus or sustained release format. The manner of fabrication of the carrier microparticle including the material of which it is made will determine how the chemotherapeutic agent is released after the particles have been delivered at or near the target tumor. Such fabrication techniques are well-documented in the patent and technical literature and need not be replicated here. Suffice it to say that any fabrication materials and procedures resulting in a desired release format are all within the scope of this invention.

As used herein, loading a chemotherapeutic drug "into or onto" a microparticle refers to (1) "into"—drug-carrying particles where the drug is encapsulated in the matrix of the particle, if it is solid, or at the core of the particle if it constitutes a core-shell structure—liposomes and polymersomes herein or (2) "onto"—drug-carrying particle where the drug is attached to the outer surface of the particle, which can be accomplished by any number of means well-known in the art.

The method of this invention can be used to treat any solid tumor cancer to which blood is supplied by a dedicated, relatively reachable artery such as the renal, hepatic, pulmonary and cardiac arteries. In particular at present it can be used to treat HCC tumors. As such, the chemotherapeutic agent(s) which may be used in the instant method include virtually all known chemotherapeutics as well as those that become available in the future.

As used herein, a "patient" refers to any species that might benefit from treatment using the method herein but at present is preferably a mammal and most preferably a human being.

What is claimed:

1. A method for delivering a chemotherapeutic agent to a malignant solid tumor in a patient, comprising;
   delivering to the patient a first plurality of biodegradable microparticles through an artery to a first location at or near the malignant solid tumor, wherein the first plurality of biodegradable microparticles comprises a chemotherapeutic agent and wherein the first plurality of biodegradable microparticles has a mean diameter of about 10 to 300 µm;
   delivering a second plurality of biodegradable microparticles through the artery to a second location proximal to the location at which the first plurality of biodegradable microparticles was delivered, wherein the second plurality of biodegradable microparticles has a mean diameter of about 900 to about 1200 µm, and wherein:
      the first plurality of biodegradable microparticles and second plurality of biodegradable microparticles are administered sequentially at different times,
      the second plurality of biodegradable microparticles is lodged in a target artery between where the first plurality of biodegradable microparticles has lodged and the heart, and
      a therapeutically effective amount of the chemotherapeutic agent is released as the first plurality of biodegradable microparticles degrades over a period of at least 6 months while the second plurality of biodegradable microparticles substantially completely cuts off the flow of blood to the tumor upon initial delivery to its location and as it degrades over the same timespan as the first plurality of biodegradable microparticles, blood flow is restored.

2. The method of claim 1, wherein the first and second plurality of biodegradable microparticles independently comprise a polymer that undergoes about 50% to about 100% mass loss in vivo at about 6 months after delivery at or near the tumor.

3. The method of claim 1, wherein the first and second plurality of biodegradable microparticles independent comprise a polymer that undergoes about 70% to about 80% mass loss in vivo at about 6 months after delivery of the microparticles at or near the tumor.

4. The method of claim 1, wherein the first plurality of biodegradable microparticles comprise liposomes.

5. The method of claim 1, wherein the first plurality of biodegradable microparticles comprise polymersomes.

6. The method of claim 1, wherein the first plurality of biodegradable microparticles comprise solid polymeric particles.

7. The method of claim 1, wherein the first and second plurality of biodegradable microparticles independently comprise a polymer selected from the group consisting of poly(D,L-lactide), poly(D,L-lactide-co-glycolide), poly(L-lactide-co-glycolide), poly(L-lactide-co-glycolide-co-ε-caprolactone) and poly(D,L-lactide-co-ethylene glycol), poly(L-lactide-co-ethylene glycol), poly(D,L-lactide-bl-glycolide), poly(L-lactide-bl-glycolide), poly(D,L-lactide-bl-ethylene glycol), poly(L-lactide-bl-glycolide), poly(D,L-lactide-bl-lycolide-bl-caprolactone), poly(L-lactide-bl-glycolide-bl-ethylene glycol, a poly(ester amide) and any combination thereof.

8. The method of claim 7, wherein the first plurality of biodegradable microparticles comprises poly(L-lactide-co-glycolide).

9. The method of claim 8, wherein the molar ratio of L-lactide to glycolide is about 3:2 to about 9:1.

10. The method of claim 8, wherein the number average molecular weight of the poly(L-lactide-co-glycolide) is about 100 kDa to about 150 kDA.

11. The method of claim 7, wherein the first plurality of biodegradable microparticles comprises a polymer comprising poly(ethylene glycol).

12. The method of claim 11, wherein the number average molecular weight of poly(ethylene glycol) in any of the poly(ethylene glycol)-containing polymers is about 500 kDa to about 10,000 kDa.

13. The method of claim 4, wherein the chemotherapeutic drug to polymer weight ratio is about 1:1 to about 1:5.

14. The method of claim 5, wherein the chemotherapeutic drug to polymer weight ratio is about 1:1 to about 1:5.

15. The method of claim 6, wherein the chemotherapeutic drug to polymer weight ratio is about 1:1 to about 1:5.

16. The method of claim 1, wherein two or more chemotherapeutic agents are loaded into or onto the same microparticles of the first plurality of biodegradable microparticles.

17. The method of claim 1, wherein two or more chemotherapeutic agents are loaded into or onto different microparticles of the first plurality of biodegradable microparticles, the different microparticles being mixed together prior to delivery at or near the tumor.

18. The method of claim 1, wherein the malignant solid tumor is a hepatocellular carcinoma.

19. The method of claim 18, wherein the chemotherapeutic agent is doxorubicin.

20. The method of claim 19, wherein the chemotherapeutic agent further comprises an agent selected from the group consisting of cisplatin and mitomycin C.

21. The method of claim 1, wherein the second plurality of biodegradable microparticles comprise solid polymeric particles.

22. The method of claim 1, wherein:
   the first plurality of biodegradable microparticles is delivered at or near the tumor prior to delivery of the second plurality of microparticles, or
   the second plurality of biodegradable microparticles is delivered at or near the tumor and the first plurality of biodegradable microparticles is subsequently injected into the artery between the tumor and where the second biodegradable plurality of microparticles have lodged in the artery.

* * * * *